(12) United States Patent
Bergmann et al.

(10) Patent No.: US 7,153,662 B2
(45) Date of Patent: Dec. 26, 2006

(54) INFLAMMATION-SPECIFIC PEPTIDES AND THE USES THEREOF

(75) Inventors: Andreas Bergmann, Berlin (DE); Joachim Struck, Berlin (DE); Monika Ühlein, Berlin (DE)

(73) Assignee: B.R.A.H.M.S. Aktiengesellschaft, Henningsdorf (DE)

( * ) Notice: Subject to any disclaimer, the term of this patent is extended or adjusted under 35 U.S.C. 154(b) by 0 days.

(21) Appl. No.: 10/476,065

(22) PCT Filed: Apr. 16, 2002

(86) PCT No.: PCT/EP02/04219

§ 371 (c)(1),
(2), (4) Date: May 13, 2004

(87) PCT Pub. No.: WO02/085937

PCT Pub. Date: Oct. 31, 2002

(65) Prior Publication Data

US 2004/0214229 A1    Oct. 28, 2004

(30) Foreign Application Priority Data

Apr. 23, 2001 (DE) ............................... 101 19 804

(51) Int. Cl.
*G01N 33/53* (2006.01)
(52) U.S. Cl. ..................... 435/7.1; 435/7.21
(58) Field of Classification Search ................... None
See application file for complete search history.

(56) References Cited

U.S. PATENT DOCUMENTS

| 5,639,617 A | 6/1997 | Bohuon ................ 435/7.1 |
| 5,660,994 A | 8/1997 | Bruder-Heid et al. ...... 435/7.23 |

FOREIGN PATENT DOCUMENTS

| DE | 198 47 690 A1 | | 4/2000 |
| EP | 0 656 121 B1 | | 3/1998 |
| WO | WO 98/11217 | | 3/1998 |
| WO | WO009811217 | * | 3/1998 |
| WO | WO 99/47669 | | 9/1999 |
| WO | WO 00/22439 | | 4/2000 |

OTHER PUBLICATIONS

Liddell, E. and Weeks, I. Antibody Technology Bios Scientific Pub Ltd, Chapter 5, p. 65-83, 1995.*
Aird, "The Hematologic System as a Marker of Organ Dysfunction in Sepsis," *Mayo Clin, Proc.*, 78:869-881, 2003.
Carrigan et al., "Toward Resolving the Challenges of Sepsis Diagnosis," *Clin. Chem.*, 50(8):1301-1314, 2004.
Hotchkiss and Karl, "The Pathophysiology and Treatment of Sepsis," *N. Engl. J. Med.*, 348(2):138-150, 2003.
Marshall et al., "Measures, Markers, and Mediators: Toward a Staging System for Clinical Sepsis. A Report of the Fifth Toronto Sepsis Roundtable, Toronto, Ontario, Canada, Oct. 25-26, 2000," *Crit. Care Med.*, 31(5):1560-1567, 2003 (Abstract only).
Oberholzer et al., "Sepsis Syndromes: Understanding the Role of Innate and Acquired Immunity," *Shock*, 16(2):83-96, 2001 (Abstract only).
Assicot, et al., "High Serum Procalcitonin Concentrations in Patients with Sepsis and Infection," *Lancet*, 341(8844):515-518, 1993.
Beishuizen et al., "Endogenous Mediators in Sepsis and Septic Shock," *Advances Clin. Chem.*, 33:55-131, 1999.
Calandra et al., "Protection from Septic Shock by Neutralization of Macrophage Migration Inhibitory Factor," *Nature Medicine*, 6(2):164-170, 2000.
Gabay and Kushner, "Acute-Phase Proteins and Other Systemic Responses to Inflammation," *New Engl. J. Med.*, 340(6):448-454, 1999.
Garber, "Protein C May Be Sepsis Solution," *Nature Biotechnology*, 18:917-918, 2000.
Ghillani et al., "Monoclonal Antipeptide Antibodies as Tools to Dissect Closely Related Gene Products," *J. Immunol.*, 141(9):3156-3163, 1988.
Ghillani et al., "Identification and Measurement of Calcitonin Precursors in Serum of Patients with Malignant Diseases," *Cancer Research*, 49(23):6845-6851, 1989.
Heukeshoven and Dernick, "Improved Silver Staining Procedure for Fast Staining in PhastSystem Development Unit. I. Staining of Sodium Dodecyl Sulfate Gels," *Electrophoresis*, 9(1):28-32, 1988.
Karzai, et al., "Procalcitonin—A New Indicator of the Systemic Response to Severe Infections," *Infection*, 25:3-8, 1997.
Klose, "Fractionated Extraction of Total Tissue Proteins from Mouse and Human for 2-D Electrophoresis," *In: Methods in Molecular Biology*, vol. 112, 2-D Proteame Analysis Protocols, Humana Press Inc., N.J., pp. 67-85.
Klose and Kobalz, "Two-Dimensional Electrophoresis of Proteins: An Updated Protocol and Implications for a Functional Analysis of the Genome," *Electrophoresis*, 16:1034-1059, 1995.
Lamerdin et al., EMBL Database Accession No. 075272.
Lingner et al., "Reverse Transcriptase Motifs in the Catalytic Subunit of Telomerase," *Science*, 276:561-567, 1997.
Mann and Pandey, "Use of Mass Spectrometry-Derived Data to Annotate Nucleotide and Protein Sequence Databases," *TRENDS Biochem. Sci.*, 26(1):54-61, 2001.
Neubauer et al., Mass Spectrometry and EST-Database Searching Allows Characterization of the Multi-Protein Spliceosome Complex, *Nature Genetics*, 20:46-50, 1998.

(Continued)

*Primary Examiner*—Prema Mertz
(74) *Attorney, Agent, or Firm*—Heslin Rothenberg Farley & Mesiti P.C.; Kathy Smith Dias (57) ABSTRACT

The invention relates to novel peptides and partial peptide sequences for the diagnosis and therapy of inflammations and sepsis, which are formed in the case of inflammations and/or infections of primates and humans, and their use or the use of antibodies formed against these peptides in diagnosis and therapy.

2 Claims, 3 Drawing Sheets

OTHER PUBLICATIONS

Oczenski et al., "Procalcitonin: A New Parameter for the Diagnosis of Bacterial Infection in the Peri-Operative Period," *Eur. J. Anaesthesiol.*, 15:202-209, 1998.

Otto et al., "Identification of Human Myocardial Proteins Separated by Two-Dimensional Electrophoresis Using an Effective Sample Preparation for Mass Spectrometry," *Electrophoresis*, 17:1643-1650, 1996.

Panacek, "Anti-TNF Strategies," *Intensive Care Med.*, 23:1144-1149, 1997.

Redl et al., "Procalcitonin Release Patterns in a Baboon Model of Trauma and Sepsis: Relationship to Cytokines and Neopterin," *Crit. Care Med.*, 28(11):3659-3663, 2000.

Redl and Schlag, "Non-Human Primate Models of Sepsis," *Sepsis*, 2:243-253, 1998.

Reinhart et al., "Sepsis Und Spetischer Schcok," *Intensivmedizin*, 756-760, 2001.

International Search Report for PCT Application Serial No. PCT/EP02/04219, mailed Oct. 11, 2002.

* cited by examiner

FIGURE 3

SEQUENCE LISTING

<160> NUMBER OF SEQ ID NOS: 5

<210> SEQ ID NO 1
<211> LENGTH: 12
<212> TYPE: PRT
<213> ORGANISM: Papio cynephalus anubis

<400> SEQUENCE: 1

Val Ser Glu Pro Thr Thr Val Ala Phe Asp Val Arg
 1               5                  10

<210> SEQ ID NO 2
<211> LENGTH: 152
<212> TYPE: PRT
<213> ORGANISM: Homo sapiens

<400> SEQUENCE: 2

Met Ala Ala Pro Ser Gly Gly Trp Asn Gly Val Gly Ala Ser Leu Trp
 1               5                  10                  15

Ala Ala Leu Leu Leu Gly Ala Val Ala Leu Arg Pro Ala Glu Ala Val
            20                  25                  30

Ser Glu Pro Thr Thr Val Ala Phe Asp Val Arg Pro Gly Gly Val Val
        35                  40                  45

His Ser Phe Ser His Asn Val Gly Pro Gly Val Arg Ala Thr Ala Asp
    50                  55                  60

Lys Tyr Thr Cys Met Phe Thr Tyr Ala Ser Gln Gly Gly Thr Asn Glu
65                  70                  75                  80

Gln Trp Gln Met Ser Leu Gly Thr Ser Glu Asp His Gln His Phe Thr
                85                  90                  95

Cys Thr Ile Trp Arg Pro Gln Gly Lys Ser Tyr Leu Tyr Phe Thr Gln
            100                 105                 110

Phe Lys Ala Glu Val Arg Gly Ala Glu Ile Glu Tyr Ala Met Ala Tyr
        115                 120                 125

Ser Lys Ala Ala Phe Glu Arg Glu Ser Asp Val Pro Leu Lys Thr Glu
    130                 135                 140

Glu Phe Glu Val Thr Lys Thr Ala
145                 150

<210> SEQ ID NO 3
<211> LENGTH: 170
<212> TYPE: PRT
<213> ORGANISM: Homo sapiens

<400> SEQUENCE: 3

Pro Ser Gly Gly Trp Asn Gly Val Gly Ala Ser Leu Trp Ala Ala Leu
 1               5                  10                  15

Leu Leu Gly Ala Val Ala Leu Arg Pro Ala Glu Ala Val Ser Glu Pro
            20                  25                  30

Thr Thr Val Ala Phe Asp Val Arg Pro Gly Gly Val Val His Ser Phe
        35                  40                  45

Ser His Asn Val Gly Pro Gly Asp Lys Tyr Thr Cys Met Phe Thr Tyr
    50                  55                  60

```
Ala Ser Gln Gly Gly Thr Asn Glu Gln Trp Gln Met Ser Leu Gly Thr
 65                  70                  75                  80

Ser Glu Asp His Gln His Phe Thr Cys Thr Ile Trp Arg Pro Gln Gly
                 85                  90                  95

Lys Ser Tyr Leu Tyr Phe Thr Gln Phe Lys Ala Glu Val Arg Gly Ala
            100                 105                 110

Glu Ile Glu Tyr Ala Met Ala Tyr Ser Lys Ala Ala Phe Glu Arg Glu
        115                 120                 125

Ser Asp Val Pro Leu Phe Thr Glu Glu Phe Glu Val Thr Lys Thr Ala
    130                 135                 140

Val Ala His Arg Pro Gly Ala Phe Lys Ala Glu Leu Ser Lys Leu Val
145                 150                 155                 160

Ile Val Ala Lys Ala Ser Arg Thr Glu Leu
                165                 170

<210> SEQ ID NO 4
<211> LENGTH: 142
<212> TYPE: PRT
<213> ORGANISM: Homo sapiens

<400> SEQUENCE: 4

Val Ser Glu Pro Thr Thr Val Ala Phe Asp Val Arg Pro Gly Gly Val
  1               5                  10                  15

Val His Ser Phe Ser His Asn Val Gly Pro Gly Asp Lys Tyr Thr Cys
             20                  25                  30

Met Phe Thr Tyr Ala Ser Gln Gly Gly Thr Asn Glu Gln Trp Gln Met
         35                  40                  45

Ser Leu Gly Thr Ser Glu Asp His Gln His Phe Thr Cys Thr Ile Trp
     50                  55                  60

Arg Pro Gln Gly Lys Ser Tyr Leu Tyr Phe Thr Gln Phe Lys Ala Glu
 65                  70                  75                  80

Val Arg Gly Ala Glu Ile Glu Tyr Ala Met Ala Tyr Ser Lys Ala Ala
                 85                  90                  95

Phe Glu Arg Glu Ser Asp Val Pro Leu Lys Thr Glu Glu Phe Glu Val
            100                 105                 110

Thr Lys Thr Ala Val Ala His Arg Pro Gly Ala Phe Lys Ala Glu Leu
        115                 120                 125

Ser Lys Leu Val Ile Val Ala Lys Ala Ser Arg Thr Glu Leu
    130                 135                 140

<210> SEQ ID NO 5
<211> LENGTH: 178
<212> TYPE: PRT
<213> ORGANISM: Homo sapiens

<400> SEQUENCE: 5

Met Ala Ala Pro Ser Gly Gly Trp Asn Gly Val Gly Ala Ser Leu Trp
  1               5                  10                  15

Ala Ala Leu Leu Leu Gly Ala Val Ala Leu Arg Pro Ala Glu Ala Val
             20                  25                  30

Ser Glu Pro Thr Thr Val Ala Phe Asp Val Arg Pro Gly Gly Val Val
         35                  40                  45

His Ser Phe Ser His Asn Val Gly Pro Gly Val Arg Ala Thr Ala Asp
     50                  55                  60

Lys Tyr Thr Cys Met Phe Thr Tyr Ala Ser Gln Gly Gly Thr Asn Glu
 65                  70                  75                  80
```

-continued

```
Gln Trp Gln Met Ser Leu Gly Thr Ser Glu Asp His Gln His Phe Thr
                85                  90                  95

Cys Thr Ile Trp Arg Pro Gln Gly Lys Ser Tyr Leu Tyr Phe Thr Gln
            100                 105                 110

Phe Lys Ala Glu Val Arg Gly Ala Glu Ile Glu Tyr Ala Met Ala Tyr
        115                 120                 125

Ser Lys Ala Ala Phe Glu Arg Glu Ser Asp Val Pro Leu Phe Thr Glu
    130                 135                 140

Glu Phe Glu Val Thr Lys Thr Ala Val Ala His Arg Pro Gly Ala Phe
145                 150                 155                 160

Lys Ala Glu Leu Ser Lys Leu Val Ile Val Ala Lys Ala Ser Arg Thr
                165                 170                 175

Glu Leu
```

INFLAMMATION-SPECIFIC PEPTIDES AND THE USES THEREOF

The present application is a nationalization of PCT application Ser. No. PCT/EP02/04219, filed Apr. 16, 2002, which claims priority to German priority application Serial No. 101 19 804.3, filed Apr. 23, 2001.

The present invention relates to novel peptides, the physiological occurrence, detection and physiological functions of which have not been described to date in the scientific literature either with regard to healthy persons or with regard to any pathological processes, and the use of such peptides and their fragments or partial peptides and functional products in medical diagnostics and therapy. The term "peptides" is used in the present application in the context of a generic term which is intended to include the condensates of amino acids independently of the length of the chain formed, i.e. in particular products which, taking into account their chain length, can be referred to as oligopeptides, polypeptides or proteins.

The present invention has its origin in intensive research work by the Applicant in relation to further improvements of the diagnosis and therapy of inflammations and infections, in particular of inflammations of infectious aetiology and sepsis.

Inflammations are defined very generally by certain physiological reactions of a organism to different types of external effects, such as, for example, injuries, burns, allergens, infections by microorganisms, such as bacteria and fungi and viruses, to foreign tissues which trigger rejection reactions, or to certain inflammatory endogenous conditions of the body, for example in autoimmune diseases and cancer. Inflammations may occur as harmless, localized reactions of the body but are also typical features of the numerous serious chronic and acute diseases of individual tissues, organs, organ parts and tissue parts.

Local inflammations are generally part of the healthy immune reaction of the body to harmful effects and hence part of the life-preserving defence mechanism of the body. If, however, inflammations are part of a misdirected reaction of the body to certain endogenous processes, such as, for example, in autoimmune diseases, and/or are of a chronic nature, or if they achieve a systemic extent, as in the case of systemic inflammatory response syndrome (SIRS) or in the case of a severe sepsis caused by infection, the physiological processes typical of inflammatory reactions go out of control and become the actual, frequently life-threatening pathological process.

It is now known that the origin and the course of inflammatory processes are controlled by a considerable number of substances which are predominantly of a protein or peptide nature or are accompanied by the occurrence of certain biomolecules for a more or less limited time. The endogenous substances involved in inflammatory reactions include in particular those which may be counted among the cytokines, mediators, vasoactive substances and acute phase proteins and/or hormonal regulators. The inflammatory reaction is a complex physiological reaction in which both the endogenous substances activating the inflammatory process (e.g. TNF-α) and deactivating substances (e.g. interleukin-10) are involved.

In systemic inflammations, as in the case of a sepsis or of septic shock, the inflammation-specific reaction cascades spread in an uncontrolled manner over the whole body and become life-threatening in the context of an excessive immune response. Regarding the current knowledge about the occurrence and the possible role of individual groups of endogenous inflammation-specific substances, reference is made, for example, to A. Beishuizen et al., "Endogenous Mediators in Sepsis and Septic Shock", Advances in Clinical Chemistry, Vol. 33, 1999, 55–131; and C. Gabay et al., "Acute Phase Proteins and Other Systemic Responses to Inflammation", The New England Journal of Medicine, Vol. 340, No. 6, 1999, 448–454. Since the understanding of sepsis and related systemic inflammatory diseases, and hence also the recognized definitions, have changed in recent years, reference is also made to K. Reinhart et al., "Sepsis und septischer Schock" [Sepsis and septic shock], in: Intensivmedizin, Georg Thieme Verlag, Stuttgart, N.Y., 2001, 756–760, where a modern definition of sepsis is given. In the context of the present application, the terms sepsis and inflammatory diseases used are based on the definitions given in the stated three references.

Whereas at least in Europe the systemic bacterial infection detectable by a positive blood culture long characterized the term sepsis, sepsis is now primarily understood as being systemic inflammation which is caused by infection but, as a pathological process, has great similarities to systemic inflammations which are triggered by other causes. Said transformation in the understanding of sepsis has resulted in changes in the diagnostic approaches. Thus, the direct detection of bacterial pathogens was replaced or supplemented by complex monitoring of physiological parameters and, more recently, in particular by the detection of certain endogenous substances involved in the sepsis process or in the inflammatory process, i.e. specific "biomarkers".

Of the large number of mediators and acute phase proteins which are known to be involved in an inflammatory process, the ones which are suitable for diagnostic purposes are in particular those whose occurrence is very specific for inflammatory diseases or certain phases of inflammatory diseases, whose concentrations change in a dramatic and diagnostically significant manner and which moreover have the stabilities required for routine determination and reach high concentration values. For diagnostic purposes, the reliable correlation of pathological process (inflammation, sepsis) with the respective biomarker is of primary importance, without there being any need to know its role in the complex cascade of the endogenous substances involved in the inflammatory process.

Such an endogenous substance particularly suitable as a sepsis biomarker is procalcitonin. Procalcitonin is a prohormone whose serum concentrations reach very high values under the conditions of a systemic inflammation of infectious aetiology (sepsis), whereas it is virtually undetectable in healthy persons. High values of procalcitonin are also reached in a relatively early stage of a sepsis, so that the determination of procalcitonin is also suitable for early diagnosis of a sepsis and for early distinguishing of a sepsis caused by infection from severe inflammations which have other causes. The determination of procalcitonin as a sepsis marker is the subject of the publication by M. Assicot et al., "High serum procalcitonin concentrations in patients with sepsis and infection", The Lancet, Vol. 341, No. 8844, 1993, 515–518; and the patents DE 42 27 454 C2 and EP 0 656 121 B1 and U.S. Pat. No. 5,639,617. Reference is hereby made to said patents and to early literature references mentioned in said publication for supplementing the present description. In recent years, the number of publications on the subject of procalcitonin has greatly increased. Reference is therefore also made to W. Karzai et al., "Procalcitonin—A New Indicator of the Systemic Response to Severe Infection", Infection, Vol. 25, 1997, 329–334; and M. Oczenski et al., "Procalcitonin: a new parameter for the diagnosis of bacterial infection in the peri-operative period", European Journal of Anaesthesiology 1998, 15, 202–209; and furthermore H. Redl et al., "Procalcitonin release patterns in a baboon model of trauma and sepsis: Relationship to cytokines and neopterin", Crit Care Med 2000, Vol. 28, No. 11, 3659–3663; and H. Redl et al., "Non-Human Primate Models of Sepsis", in: Sepsis 1998; 2:243–253; and the further literature references cited therein, as typical of recent published reviews.

The availability of the sepsis marker procalcitonin has given considerable impetus to sepsis research, and intensive efforts are now being made to find further biomarkers which can supplement the procalcitonin determination and/or are capable of providing additional information for purposes of fine diagnosis or differential diagnosis. The search for potential new sepsis biomarkers is however complicated by the fact that frequently very little or nothing is known about the exact function or about the exact reasons for the occurrence of certain endogenous substances which are involved in inflammatory or septic processes.

The results of the experimental testing of a fruitful purely hypothetical approach to the determination of further potential sepsis markers are to be found in DE 198 47 690 A1 and WO 00/22439. There, it is shown that, in the case of sepsis, not only is the concentration of the prohormone procalcitonin increased but also significantly increased concentrations can be observed for other substances which may be included among the peptide prohormones. While the phenomenon described is well documented, the causes of the increase in the concentrations of prohormones in sepsis are still substantially unexplained.

In the present application, an initial result of another, purely experimental approach in the search for further inflammation- or sepsis-specific biomolecules is now reported. These experimental investigations, too, originate in the determination of procalcitonin in relation to systemic inflammatory reactions of infectious aetiology. Thus, it had been observed at a very early stage that the procalcitonin is evidently not formed in the same manner in sepsis as when it is a precursor for the hormone calcitonin. Thus, high procalcitonin levels were also observed in patients whose thyroid had been removed. The thyroid therefore cannot be the organ in which procalcitonin is formed or secreted during sepsis. In the publications by H. Redl et al., "Procalcitonin release patterns in a baboon model of trauma and sepsis: Relationship to cytokines and neopterin", Crit Care Med 2000, Vol. 28, No. 11, 3659–3663; and H. Redl et al., "Non-Human Primate Models of Sepsis", Sepsis 1998; 2:243–253, the results of experimental investigations which are said to be intended for explaining the formation of procalcitonin in sepsis are reported. In said work, an artificial sepsis is produced by endotoxin administration to primates (baboons), and the experimentally produced states in which the highest procalcitonin concentrations in the blood are reached are determined. A further development of the experimental animal model described in said work serves, in the context of the present application, for determining novel endogenous sepsis-specific biomarkers of a peptic or protein nature, the occurrence of which is characteristic for sepsis or certain forms of sepsis and which therefore permit a specific diagnosis of sepsis. The primate model was chosen because of the very great similarity of the physiology of primates and humans and the high cross-reactivity with many therapeutic and diagnostic human reagents.

Since the endogenous substances formed during inflammations are part of the complex reaction cascade of the body, not only are said substances also of diagnostic interest but attempts are currently also being made, with considerable effort, to intervene therapeutically in the inflammatory process by influencing the formation and/or the concentration of individual substances of this type, in order to stop as early as possible the systemic spread of the inflammation, which spread is observed, for example, during sepsis. In this context, endogenous substances which have been shown to be involved in the inflammatory process are also regarded as potential therapeutic targets. Attempts based on certain mediators of the inflammatory process and intended to have a positive therapeutic influence on said process are described, for example, in E. A. Panacek, "Anti-TNF strategies", Journal für Anästhesie und Intensivbehandlung"; No. 2, 2001, 4–5; T. Calandra et al., "Protection from septic shock by neutralization of macrophage migration inhibitory factor", Nature Medicine, Vol. 6, No. 2, 2000, 164–170; or K. Garber, "Protein C may be sepsis solution", Nature Biotechnology, Vol. 18, 2000, 917–918. These therapeutic approaches are intended to lower the concentrations of inflammation-promoting substances or to inhibit the formation of said substances, and to do so in particular with the use of specific antibodies (against TNF-α or MIF; cf. E. A. Panacek, "Anti-TNF strategies", Journal für Anästhesie und Intensivbehandlung; No. 2, 2001, 4–5; T. Calandra et al., "Protection from septic shock by neutralization of macrophage migration inhibitory factor", Nature Medicine, Vol. 6, No. 2, 2000, 164–170) or to increase the concentration of endogenous substances which have an inhibitory effect in the inflammation cascade (Protein C; K. Garber, "Protein C may be sepsis solution", Nature Biotechnology, Vol. 18, 2000, 917–918). The last-mentioned publication gives an overview of such attempts to have a therapeutic influence on the inflammatory process by influencing selected endogenous target molecules, which attempts have unfortunately generally met with little success to date. In view of the rather disappointing therapeutic approaches to date, there is great interest in identifying further endogenous biomolecules which are as inflammation- or sepsis-specific as possible and which, as therapeutic targets, also open up new prospects for success in fighting inflammation.

The present invention provides novel peptides which are formed in primates and humans during inflammations caused by infection and are suitable both for inflammation diagnosis/sepsis diagnosis and as novel therapeutic targets.

The present invention discloses peptide sequences and their fragments which, on the basis of their specific occurrence after artificial triggering of sepsis by endotoxin administration to primates, have proved to be sequences of sepsis-specific or inflammation-specific human peptides.

Claims 1, 2 and 3 relate to these purified or isolated peptide sequences and characteristic partial sequences or fragments and fusion products thereof. Claims 4 to 6 single out particular forms of the peptides.

Uses which arise from the detected sepsis specificity are stated in claims 7 to 13. Claims 15 to 18 relate to antibodies against the peptides according to the invention and pharmaceutical compositions containing such antibodies.

As will be described in more detail below in the experimental section, the invention is based on the fact that, after experimental triggering of an artificial sepsis in baboons by endotoxin administration (LPS from *Salmonella Typhimurium*) and working-up of liver tissue of the treated animals by 2D gel electrophoresis, it was possible to find a peptide or protein product which is identifiable only in the treated animals. This specific product was isolated from the electrophoresis gel and investigated by mass spectrometry in a manner known per se. A partial sequence of 12 amino acids (SEQ ID NO:1) could be unambiguously identified and, by comparison of the sequence of this partial peptide with the data of a redundant human database containing protein sequences, the sequence could be identified as part of only two of all peptide sequences stored in the database. Both evidently belong to the same hypothetical protein (R33729_1), for which the associated genome DNA is localized on chromosome 19 according to the available database information. Nothing has been published to date on the actual occurrence of such a protein or peptide and its possible functions. Unambiguous identification of this so far only hypothetical protein as a sepsis protein is of considerable scientific, diagnostic and therapeutic interest. The Applicant coined the designation "preinflammin" for this protein and proposes this term as a designation for the future naming of said protein. The shorter peptide found directly in the course of the below-described gel electrophoretic working-up and having a lower molar mass, which is presumably to be regarded as the actual marker peptide, is accordingly designated as "inflammin".

The present invention seeks on the one hand, protection for a peptide which is unambiguously defined by the presence of the partial sequence of 12 amino acids (SEQ ID NO:1) and is distinguishable from all other known peptides and proteins without there being intended to be any restrictions with regard to the length and nature of further amino acid sequences, and on the other hand, for the complete peptide preinflammin (SEQ ID NO:5) and, the shorter marker peptide inflammin (SEQ ID NO:4) and the fragments (partial sequences) thereof which are suitable for diagnostic and/or therapeutic purposes, including fusion products which may contain the respective complete peptide or partial sequences thereof, without such partial sequences necessarily also comprising the partial sequence SEQ ID NO:1. Partial sequences in the context of the use of this term in the present application are also to be regarded as those sequences which are obtained after deletion of one or more amino acids or short peptide sequences, e.g. of a pentapeptide corresponding to the positions 59 to 63 from the total peptide SEQ ID NO:5, or from the peptide SEQ ID NO:4. Furthermore, partial sequences (fragments) suitable for diagnostic and/or therapeutic purposes are in particular those which comprise a sequence of at least three amino acids, preferably at least 6 amino acids, of the peptide SEQ ID NO:4 or corresponding parts of the amino acid sequence between the positions 32 and 178 of SEQ ID NO:5. Partial sequences in the context of use of this term in the present descriptions can also be present as parts of the peptides which are formed by exchange and/or deletion of individual amino acids or peptide fragments of the peptides according to SEQ ID NO:1, SEQ ID NO:4 and SEQ ID NO:5 and are at least 60% homologous, in particular at least 80% homologous, with one of said peptides. The peptides according to the invention may also be mammalian peptides which are at least 60% homologous with one of the peptides with SEQ ID NO:1, SEQ ID NO:4 or SEQ ID NO:5 and are used, for example, for diagnostic purposes or in veterinary medicine.

Owing to the sequence now known and the physiological role of said peptides, these can be prepared synthetically or by genetic engineering as recombination products for diagnostic and/or therapeutic purposes by methods which are now part of the prior art.

Furthermore, said peptides or suitable partial sequences thereof can be used by known methods of the modern prior art also for producing specific polyclonal and in particular monoclonal antibodies which are suitable as aids for the diagnostic determination of the peptides according to the invention and/or also as potential therapeutic agents. The production of suitable monoclonal antibodies against known peptide partial sequences is now part of a general prior art.

In the determination of inflammin or of selected partial peptides thereof, it is possible in principle to proceed as described, for example, for selective procalcitonin determination in P. P. Ghillani et al., "Monoclonal antipeptide antibodies as tools to dissect closely related gene products", The Journal of Immunology, Vol. 141, No. 9, 1988, 3156–3163; and P. P. Ghillani et al., "Identification and Measurement of Calcitonin Precursors in Serum of Patients with Malignant Diseases", Cancer Research, Vol. 49, No. 23, 1989, 6845–6851; reference also being made expressly and additionally to the immunization techniques described there, which constitute one possibility for obtaining monoclonal antibodies also against partial sequences of inflammin. Variations of the techniques described and/or further immunization techniques can be taken from relevant standard works and publications and applied in context by a person skilled in the art.

Furthermore, antibody production using techniques for direct genetic immunization with DNA should also be mentioned. It is also within the scope of the present invention to use, for example, a cDNA of the desired inflammin peptide for immunization, since it has been found in the past that the spectrum of the obtainable antibodies can be extended by such immunization techniques. Inflammin according to SEQ ID NO:4 or partial peptides thereof, for example those which contain the partial sequence SEQ ID NO:1 and/or other partial sequences, can, on the basis of the available results, serve as specific marker peptides (biomarkers) for diagnosis and for monitoring of the course of inflammations and infections (in particular of systemic infections of the sepsis type). Like the determination of procalcitonin, the determination of inflammin can be effected by the use of a method for the early differential diagnosis and for the diagnosis and for the assessment of the severity and for the therapy-accompanying assessment of the course of sepsis and infections, in such a method, the content of inflammin or of a partial peptide thereof being determined in the sample of a biological fluid or of a tissue of a patient and the presence of an inflammation, of a severe infection or of a sepsis being concluded from the established presence and/or amount of the specific peptide and the result obtained being correlated with the severity of the sepsis and possibilities for treatment and/or the prospects of treatment being estimated.

Instead of the determination of the peptides preinflammin or inflammin or their fragments or any posttranslationally modified forms thereof, the determination of the associated mRNA is also possible for diagnostic purposes.

Inflammin or its fragments or fusion products or the DNA coding therefor can also be used in preventive medicine or therapy. Thus, for example, suitable inflammin fragments can be used for the in vivo production of inflammin-binding antibodies by active immunization by techniques known per se. Those molecules which contain the complete inflammin or suitable partial sequences thereof in posttranslationally modified form, e.g. in glycosylated or phosphorylated form or in a form substituted by pharmaceutical excipients, e.g. polyethylene glycol radicals, are also to be regarded as inflammin. Furthermore, the inflammin may be present in oxidized form with a disulphide bridge formed from the two cysteine residues present or in reduced form. Inflammin or suitable partial sequences thereof may also serve as the target for therapeutic interventions in the sense that, by means of suitable specific binders for inflammin or partial peptides thereof, inflammin is deactivated intracorporeally or optionally is also eliminated extracorporeally in the sense of a "systemic lavage" or plasmapheresis with the use of suitable immunosorbents. In particular, specific antibodies, especially humanized monoclonal antibodies, are suitable for the in vivo deactivation of inflammin. However, the inflammation cascade can also be therapeutically influenced with the use of inflammin itself or of inflammin agonists or antagonists. Such therapeutic interventions are possible in particular when further discoveries about the physiological function of inflammin have been confirmed. It therefore cannot at present be ruled out that inflammin or a partial peptide thereof plays an important role in the inflammatory process, possibly as a mediator or as a hormonal regulator.

The discovery and identification of inflammin are described in more detail below, reference being made to the attached sequence listing and parts thereof. The figures show the following.

1. Infection Simulation by Endotoxin Administration in an Animal Model (Baboons)

On the basis of the experiments carried out with baboons for the stimulation of procalcitonin secretion by endotoxin injections (cf. H. Redl et al., "Procalcitonin release patterns in a baboon model of trauma and sepsis: Relationship to cytokines and neopterin", Crit Care Med 2000, Vol. 28, No. 11, 3659–3663; H. Redl et al., "Non-Human Primate Models of Sepsis", in: Sepsis 1998; 2:243–253), baboons (male, about 2 years old, weighing from 27 to 29 kg) were each intravenously administered 100 μg of LPS (lipopolysaccharide from *Salmonella Typhimurium*, source: Sigma) per kg body weight. From 5 to 5.5 h after the injection, the animals were sacrificed by intravenous administration of 10 ml of doletal. Within 60 min of their death, all organs/tissues were dissected and were stabilized by freezing in liquid nitrogen.

During the further processing, 1.5 ml of buffer A (50 mM tris/HCl, pH 7.1, 100 mM KCl, 20% of glycerol) were added to samples of the individual frozen tissues (1 g) while cooling with nitrogen, and the samples were pulverized in a porcelain mortar to give a powder (cf. J. Klose, "Fractionated Extraction of Total Tissue Proteins from Mouse and Human for 2-D Electrophoresis", in: Methods in Molecular Biology, Vol. 112: 2-D Proteome Analysis Protocols, Humana Press Inc., Totowa, N.J.). After subsequent centrifuging for 1 hour at 100,000 g and +4° C., the supernatant obtained was recovered and was stored at −80° C. until required for further processing.

Using the tissue extracts obtained in this manner, an investigation was first carried out to determine in which of the tissues investigated the largest amounts of the known sepsis biomarker procalcitonin can be produced by endotoxin administration. In the determined tissue having the highest level of procalcitonin formation, further previously unidentified protein products which occurred only after endotoxin administration were then sought by means of differential proteome analysis. For this purpose, tissue samples of untreated baboons were used as control tissue samples, the sacrificing and obtaining of samples having been effected under conditions identical to those in the case of the treated animals.

2. Determination of Baboon Tissues Having the Highest Level of Procalcitonin Formation after Endotoxin Injection Samples of the individual tissues were investigated with the aid of an immunoluminometric test which operates (similarly to the LU-MItest® PCT of the Applicant, developed for the determination of human procalcitonin) with, on the one hand, an antibody against baboon calcitonin, immobilized on polystyrene tubes, and a monoclonal antibody marked with an acridinium ester and directed against the N-terminus of baboon procalcitonin. With the aid of this test, the contents of baboon procalcitonin in the individual samples were determined after calibration of the test using recombinant human procalcitonin.

The experiments showed that liver tissue gives the largest amount of procalcitonin. The protein extracts from baboon liver which were obtained in the manner described at the outset were therefore used for searching for novel sepsis-specific biomarkers.

3. Proteome Analysis Using Cytoplasmic Liver Cell Proteins of Baboons

Cytoplasmic liver cell protein extracts of, on the one hand, healthy baboons (control) and, on the other hand, baboons which had been injected with LPS were used in a proteome analysis. In the initial analytical 2D gel electrophoresis, liver extract containing 100 pg of protein was stabilized to 9M urea, 70 mM DTT, 2% ampholyte pH 2–4 and then separated by means of analytical 2D gel electrophoresis, as described in J. Klose et al., "Two-dimensional electrophoresis of proteins: An updated protocol and implications for a functional analysis of the genome", Electrophoresis 1995, 16, 1034–1059. The visualization of the proteins in the 2D electrophoresis gel was effected by means of silver staining (cf. J. Heukeshoven et al., "Improved silver staining procedure for fast staining in Phast-System Development Unit. I. Staining of sodium dodecyl gels", Electrophoresis 1988, 9, 28–32).

For evaluation, the protein spot patterns of the samples of untreated animals were compared with the protein spot patterns which resulted from liver tissue samples of treated animals. Substances which occurred in no control sample but additionally in all treated animals were selected for further analytical investigations. FIG. 1 shows a comparison of the 2D electrophoresis gels for a control sample (A) and a sample of a treated animal (B), the additional protein spot in (B) corresponding to inflammin, the position of which is singled out by an arrow and a circle.

The novel specific proteins identified in the protein spot pattern of the analytical 2D gel electrophoresis were then prepared by means of preparatory 2D gel electrophoresis using 350 μg of protein (once again cf. (10)). In the preparative 2D gel electrophoresis, the staining was effected by means of Coomassie Brilliant Blue G250 (cf. V. Neuhoff et al., "Improved staining of proteins in polyacrylamide gels including isoelectric focusing gels with clear background at nanogram sensitivity using Coomassie Brilliant Blue G-250 and R-250", Electrophoresis 1988, 9, 255–262).

The protein spots preselected for the further analysis were cut out of the gel, using the method which is described in A. Otto et al., "Identification of human myocardial proteins separated by two-dimensional electrophoresis using an effective sample preparation for mass spectrometry", Electrophoresis 1996, 17, 1643–1650, trypsin-digested and then analyzed by mass spectroscopy, in particular with the use of mass spectrometric investigations as described and discussed, for example, in G. Neubauer et al., "Mass spectrometry and EST-database searching allows characterization of the multi-protein spliceosome complex", in: nature genetics vol. 20, 1998, 46–50; J. Lingner et al., "Reverse Transcriptase Motifs in the Catalytic Subunit of Telomerase", in: Science, Vol. 276, 1997, 561–567; M. Mann et al., "Use of mass spectrometry-derived data to annotate nucleotide and protein sequence databases", in: TRENDS in Biochemical Sciences, Vol. 26, 1, 2001, 54–61. After an ESI (Electro-SprayIonization), the trypsin-digested samples were subjected to tandem mass spectrometry. A Q-TOF mass spectrometer having a so-called nanoflow-Z-Spray ion source from Micromass, UK, was used. The procedure corresponded to the working instructions of the equipment manufacturer.

4. Identification of Inflammin

Figure 1A:
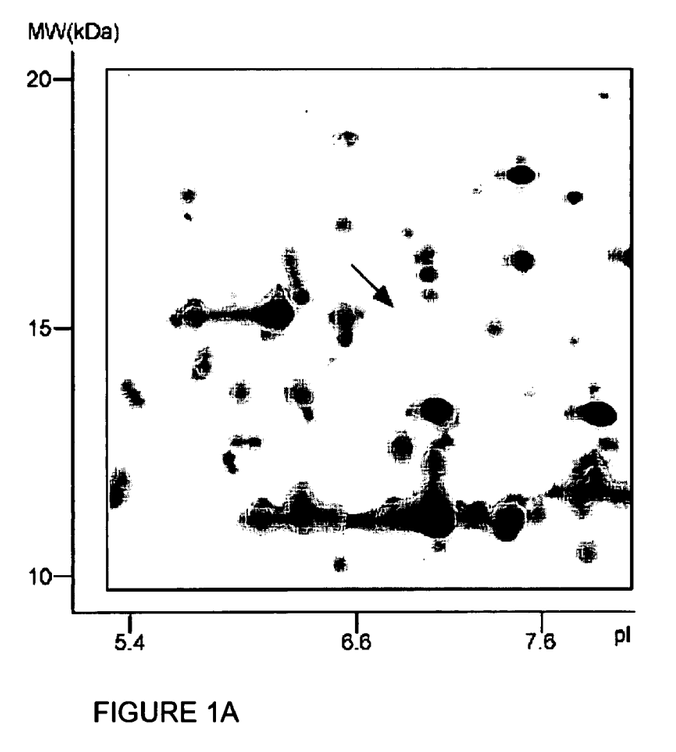
FIG. 1 shows views of 2D electrophoresis gels which permit a comparison of the spot patterns of cytoplasmic liver cell protein of a healthy baboon (A) with the liver cell proteins of a baboon 5 h after a sepsis induced by LPS administration (B). The arrow indicates the position of the sepsis-specific product according to the invention, inflammin, which is distinguished in diagram (B) by a circle.
Figure 1B:
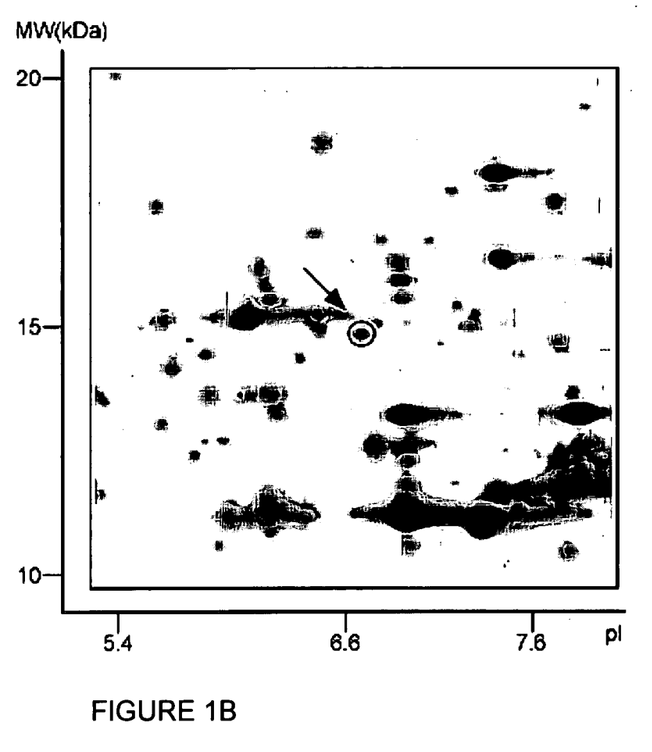

As shown in FIGS. 1(A) and 1(B), liver cell extracts of baboons to which an LPS injection had been administered contained, inter alia, a novel protein for which a molecular weight of about 15,000±700 Dalton was estimated on the basis of the gel electrophoresis data in comparison with marker substances of known molecular weight, while an isoelectric point of about 6.5 to 7 was estimated from the relative position of the protein from the first dimension.

Figure 2:
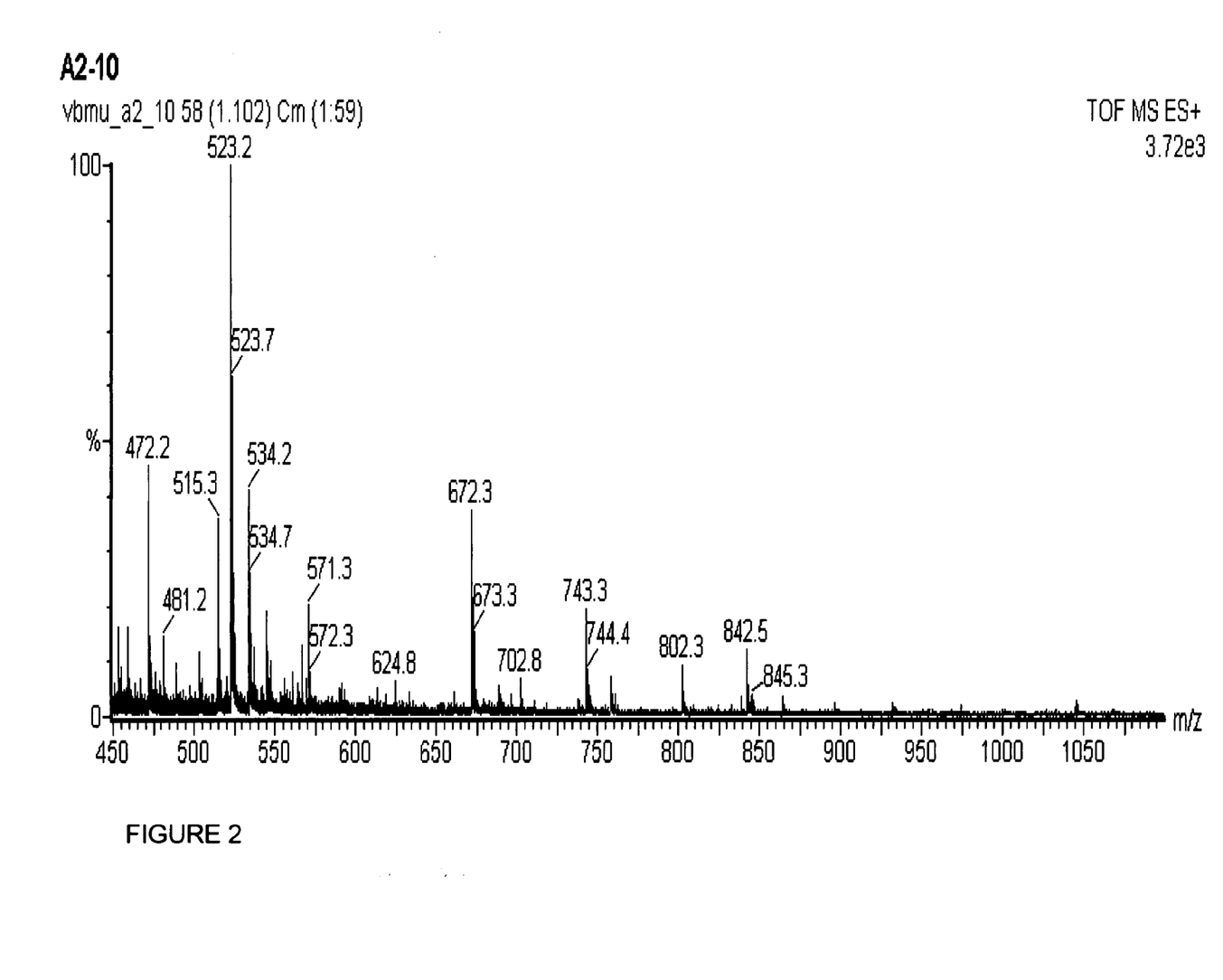
FIG. 2 shows the mass spectrum of the trypsin-digested complete product inflammin identified by 2D gel electrophoresis.
Figure 3:
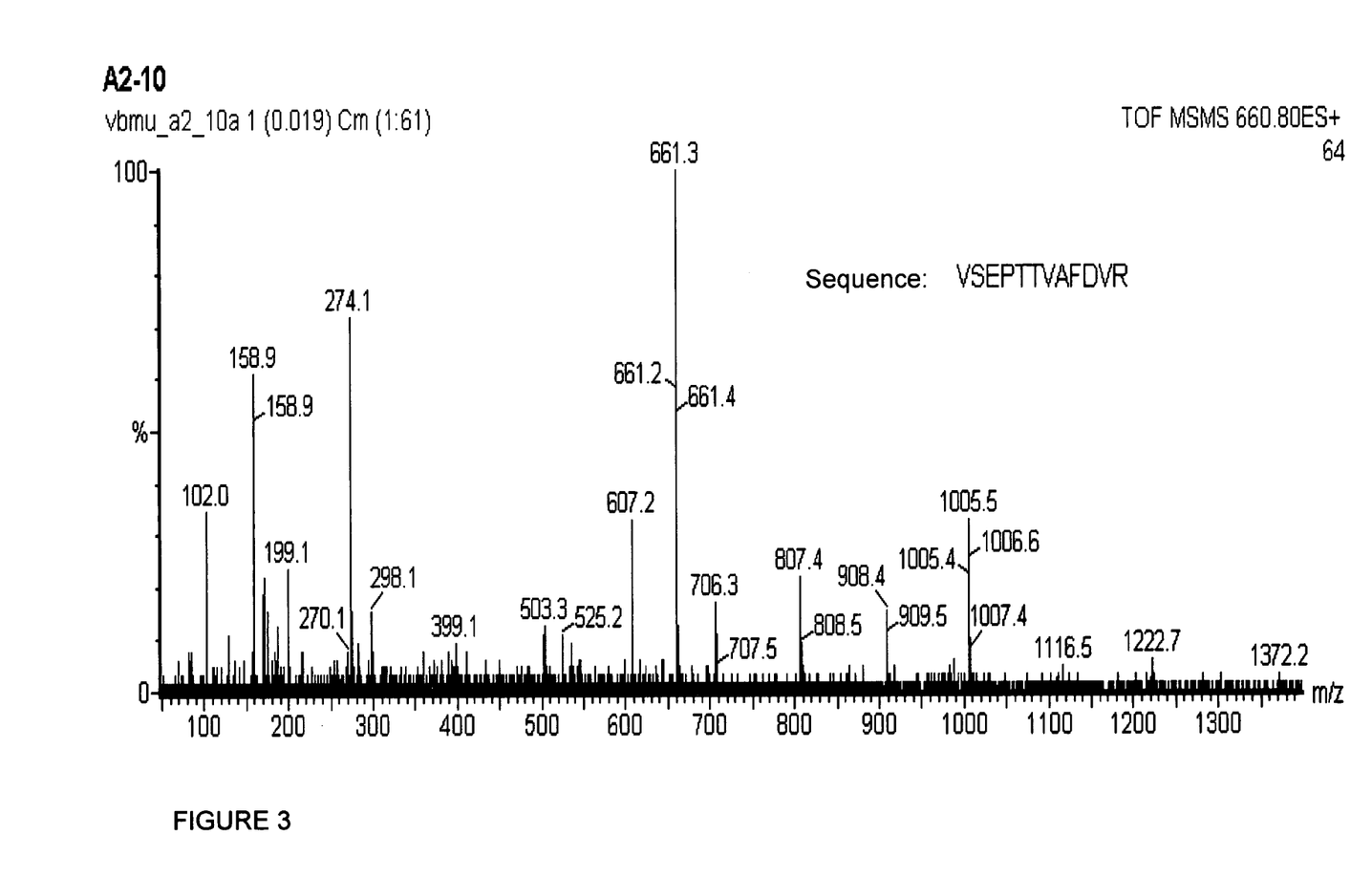
FIG. 3 shows the results of a tandem electrophoresis of a selected peptide fragment of the trypsin digestion with a charge/mass ratio of 660.80.

This protein was analyzed by mass spectrometry as above, FIG. 2 showing the mass spectrum of the total trypsin-digested protein while FIG. 3 shows the spectrum of the fragments selected by tandem mass spectroscopy and having a mass/Z of 660.8. The mass spectrum obtained for this fragment could be assigned computationally in a manner known per se to the partial sequence SEQ ID NO:1. This partial sequence was then compared with protein sequences which were available in sequence databases. In the redundant database NCBI no. 2.13.2001, two sequences in which 100% of the fragment according to SEQ ID NO:1 occurs were determined. The two sequence segments can be assigned to a hypothetical protein R33729_1 from the human genome project, one sequence (SEQ ID NO:2) being a partial sequence having 152 amino acids (AAC33800; DBSOURCE locus AC005594; Accession AC005594.1) with the designation "partial CDS", while the second partial sequence (SEQ ID NO:3) is a sequence having 170 amino acids (Locus CAB96947; DBSOURCE embl locus IR1875335; accession AL365373.1) with the designation "hypothetical protein". Both sequences are parts of a hypothetical human protein, the coding sequence of which is present on chromosome 19. The first partial sequence ("partial CDS") is sequence SEQ ID NO:2 stated in the sequence listing, while the second partial sequence is the sequence according to sequence listing SEQ ID NO:3. The partial sequence SEQ ID NO:2 contains the start codon (positions 1–3) of the total hypothetical protein, while the second partial sequence SEQ ID NO:3 contains additional amino acids before a stop codon (positions 145–170), so that the total protein SEQ ID NO:5 produced by ribosomes can be represented by combining the two sequences. The only deviation within the two sequences SEQ ID NO:2 and SEQ ID NO:3 is a pentapeptide in the position 59 to 63 of sequence SEQ ID NO:2, which has no counterpart in the second partial sequence. SEQ ID NO:2 is based on a theoretical exon/intron prediction of genomic DNA, while SEQ ID NO:3 is derived from a cDNA. Four similar mouse cDNAs (BAB25579, BAB25931, BAB23155, BAB31038) contain no corresponding pentapeptide sequence, as in the case of human cDNA. Thus, it is probable that the human polypeptide found does not contain this pentapeptide sequence. Even if it is assumed that said pentapeptide is absent, however, the theoretical molar mass of SEQ ID NO:5 (about 19 kDa) is above the value actually found for the novel protein spot (15±0.7 kDa). Checking of SEQ ID NO:5 in a prediction program for N-terminal signal sequences which may be responsible for the extracellular localization of polypeptides showed that, with high probability, the first 31 amino acids of SEQ ID NO:5 represent a signal sequence which is cleaved from the signal peptidase on translocation of the nascent polypeptide across the membrane of the endoplasmic reticulum. Such a shortening would be in good agreement with the molar mass actually observed in gel electrophoresis. An identical analysis with the above-mentioned similar mouse sequences gives an analogous prediction. Experimental evidence of the shortening is the detection of the peptide SEQ ID NO:1. This was identified by mass spectrometry after treatment of the novel protein spot from the gel electrophoresis with trypsin. The fact that, in SEQ ID NO:1, no basic amino acid is present in the position on the N-terminal side of SEQ ID NO:5, as would be typical for a trypsin digestion, is of importance. On the other hand, the cut found corresponds exactly to a cut as would be expected under the action of the signal peptidase. The protein (peptide) SEQ ID NO:5 should therefore be designated as preinflammin, while SEQ ID NO:4 is proposed for the putative mature inflammin. SEQ ID NO:4 differs from SEQ ID NO:5 in that its positions 1–31 and 59–63 are missing.

Neither has one of said proteins as such been described to date nor has it been possible to date to assign known peptides or peptide hormone fragments to such a protein. It is thus to be designated as a novel protein (or peptide), the expression of which was observed for the first time after contact of the primate organism with the administered endotoxins. To date, it is only possible to speculate about the natural role of the protein. It may be a precursor of a biologically active unknown substance (e.g. of a prohormone, having target sequences with and/or without amino-terminal methionine). Its identification for the first time and the documented high specificity make it a promising diagnostic target and a novel interesting target for therapeutic intervention.

The known complete sequence permits, for diagnostic and/or therapeutic purposes, specific preparation of the total peptide or any partial sequences (fragments) thereof, in particular using known synthetic or genetic engineering methods for the preparation of peptides. Such peptides may then serve, for example analogously to the procedure described in P. P. Ghillani et al., "Monoclonal antipeptide antibodies as tools to dissect closely related gene products", The Journal of Immunology, Vol. 141, No. 9, 1988, 3156–3163; and P. P. Ghillani et al., "Identification and Measurement of Calcitonin Precursors in Serum of Patients with Malignant Diseases", Cancer Research, Vol. 49, No. 23, 1989, 6845–6851, for the provision of suitable antibodies, in particular monoclonal antibodies, which in turn make it possible to provide assays for the immunodiagnostic determination of inflammin or selected partial peptides thereof.

Monoclonal antibodies obtainable in the known manner described can, particularly after humanization known per se, also serve for the development of novel therapeutic agents (cf. the therapeutic approaches summarized in K. Garber, "Protein C may be sepsis solution", Nature Biotechnology, Vol. 18, 2000, 917–918). Furthermore, an in vivo neutralization of inflammin is also possible by blocking of the expression of the inflammin gene.

It is furthermore within the scope of the present invention to use inflammin itself or partial peptides thereof as pharmaceutical active substances. The invention accordingly also relates to pharmaceutical compositions which contain, as the actual active substance, one of the peptides according to the invention or antibodies produced against these peptides and worked up for administration to patients, together with a suitable pharmaceutical carrier.

The invention claimed is:

1. A method for diagnosis of sepsis and/or sepsis-like systemic infections in a patient, comprising testing a biological sample from said patient for the presence of a peptide comprising the sequence of SEQ ID NO.: 4 or SEQ ID NO.: 5 or a partial sequence thereof, wherein said partial sequence comprises the amino acid sequence of SEQ ID NO:1 and wherein the presence of said peptide is indicative of the presence of sepsis and/or sepsis-like systemic infection.

2. The method according to claim 1, wherein the presence of said peptide in said biological sample is detected by binding of an antibody that binds specifically to said peptide.

* * * * *

UNITED STATES PATENT AND TRADEMARK OFFICE
CERTIFICATE OF CORRECTION

| | | |
|---|---|---|
| PATENT NO. | : 7,153,662 B2 | Page 1 of 1 |
| APPLICATION NO. | : 10/476065 | |
| DATED | : December 26, 2006 | |
| INVENTOR(S) | : Bergmann et al. | |

It is certified that error appears in the above-identified patent and that said Letters Patent is hereby corrected as shown below:

On Title Page (73)
Assignee: delete "B.R.A.H.M.S. Aktiengesellschaft" and replace with -- B.R.A.H.M.S Aktiengesellschaft --

In the specification delete the following:

Col. 4, line 50 to line 57

Signed and Sealed this

Twelfth Day of June, 2007

JON W. DUDAS
*Director of the United States Patent and Trademark Office*